US010377557B1

(12) United States Patent
Edmond

(10) Patent No.: US 10,377,557 B1
(45) Date of Patent: Aug. 13, 2019

(54) AEROSOLIZED DISINFECTANT ASSEMBLY

(71) Applicant: John Edmond, Marietta, GA (US)

(72) Inventor: John Edmond, Marietta, GA (US)

(*) Notice: Subject to any disclaimer, the term of this patent is extended or adjusted under 35 U.S.C. 154(b) by 0 days.

(21) Appl. No.: 15/936,843

(22) Filed: Mar. 27, 2018

(51) Int. Cl.

| | |
|---|---|
| ***B65D 83/20*** | (2006.01) |
| ***B65D 83/24*** | (2006.01) |
| ***B65D 83/38*** | (2006.01) |
| ***A61L 2/22*** | (2006.01) |
| ***A61L 9/14*** | (2006.01) |

(52) U.S. Cl.
CPC .............. *B65D 83/384* (2013.01); *A61L 2/22* (2013.01); *A61L 9/14* (2013.01); *B65D 83/207* (2013.01); *B65D 83/24* (2013.01); *A61L 2209/134* (2013.01); *A61L 2209/21* (2013.01)

(58) Field of Classification Search
CPC .... B65D 83/24; B65D 83/384; B65D 83/207; B05B 1/1654; A62L 2/22; A62L 9/14; A62L 2209/134; A62L 2209/21
USPC ............................................ 222/645, 402.14
See application file for complete search history.

(56) References Cited

U.S. PATENT DOCUMENTS

| | | | | |
|---|---|---|---|---|
| 2,910,391 A * | 10/1959 | Toulmin, Jr. | A47L 15/0055 | 134/25.2 |
| 3,081,918 A * | 3/1963 | Scoggin, Jr. | B65D 83/20 | 222/402.14 |
| 3,154,223 A * | 10/1964 | Messmer | B65D 83/20 | 222/402.14 |
| 5,450,983 A * | 9/1995 | Stern | B05B 1/02 | 222/1 |
| 6,152,335 A * | 11/2000 | Stern | B05B 1/02 | 222/394 |
| 7,278,590 B1 * | 10/2007 | Greer, Jr. | B05B 1/02 | 239/337 |
| 7,374,068 B2 * | 5/2008 | Greer, Jr. | B65D 83/306 | 222/1 |
| 8,608,032 B2 | 12/2013 | Wolosuk | | |
| 9,511,162 B2 | 12/2016 | Schwartz et al. | | |
| 2005/0112022 A1 | 5/2005 | Morgan | | |
| 2006/0078461 A1 | 4/2006 | Kaplan | | |
| 2008/0089817 A1 | 4/2008 | Cacciabaudo | | |
| 2009/0272025 A1 | 11/2009 | Wolosuk | | |

* cited by examiner

*Primary Examiner* — Jeremy Carroll

(57) ABSTRACT

An aerosolized disinfectant assembly for automatically disinfecting a room with an aerosolized disinfectant includes an aerosol that includes a chemical disinfectant. A canister is provided and the aerosol is contained under pressure within the canister. A fogger is coupled to the canister and the fogger is in fluid communication with an interior of the canister. The fogger is positionable in an open position thereby facilitating the aerosol to be released from the canister and into the room. In this way the chemical disinfectant is distributed around the room to disinfect the room.

8 Claims, 4 Drawing Sheets

AEROSOLIZED DISINFECTANT ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to disinfectant devices and more particularly pertains to a new disinfectant device for automatically disinfecting a room with an aerosolized disinfectant.

BRIEF SUMMARY OF THE INVENTION

An embodiment of the disclosure meets the needs presented above by generally comprising an aerosol that includes a chemical disinfectant. A canister is provided and the aerosol is contained under pressure within the canister. A fogger is coupled to the canister and the fogger is in fluid communication with an interior of the canister. The fogger is positionable in an open position thereby facilitating the aerosol to be released from the canister and into the room. In this way the chemical disinfectant is distributed around the room to disinfect the room.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
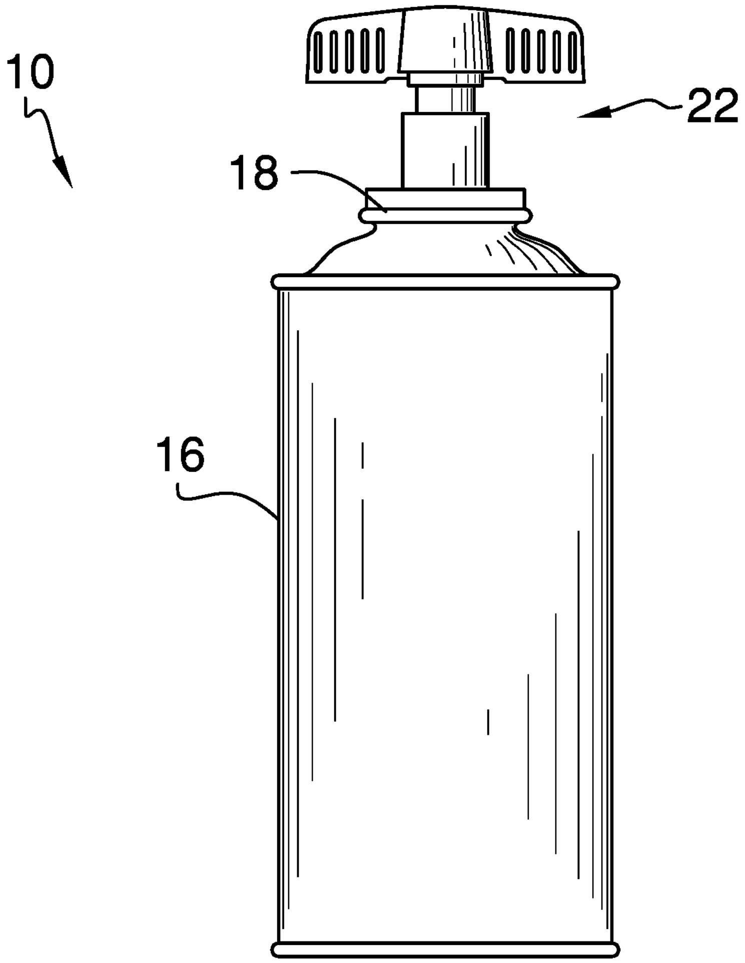
FIG. 1 is a front view of an aerosolized disinfectant assembly according to an embodiment of the disclosure.
Figure 2:
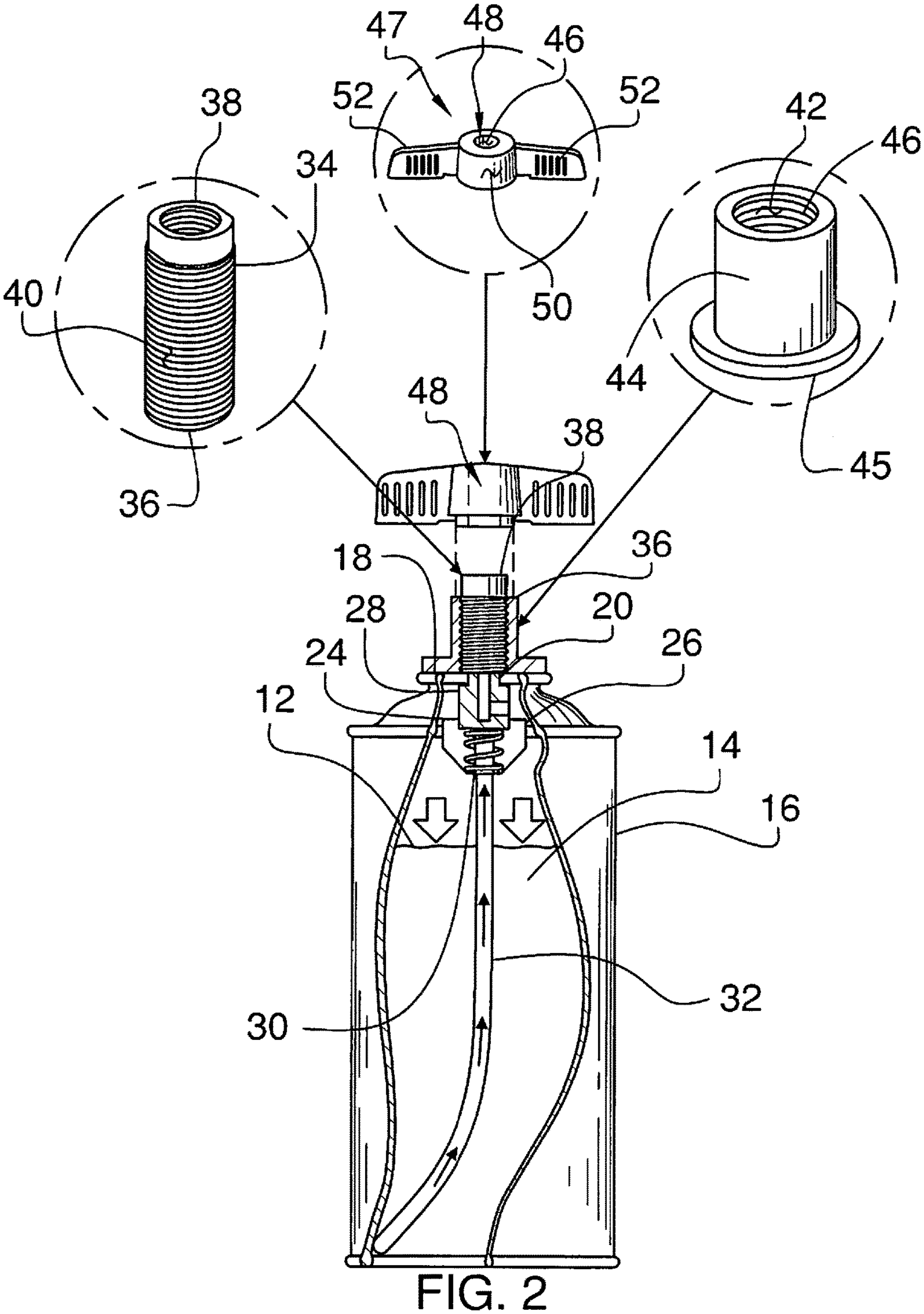
FIG. 2 is a front cut-away view of an embodiment of the disclosure showing an exhaust portion of a valve in a closed position.
Figure 3:
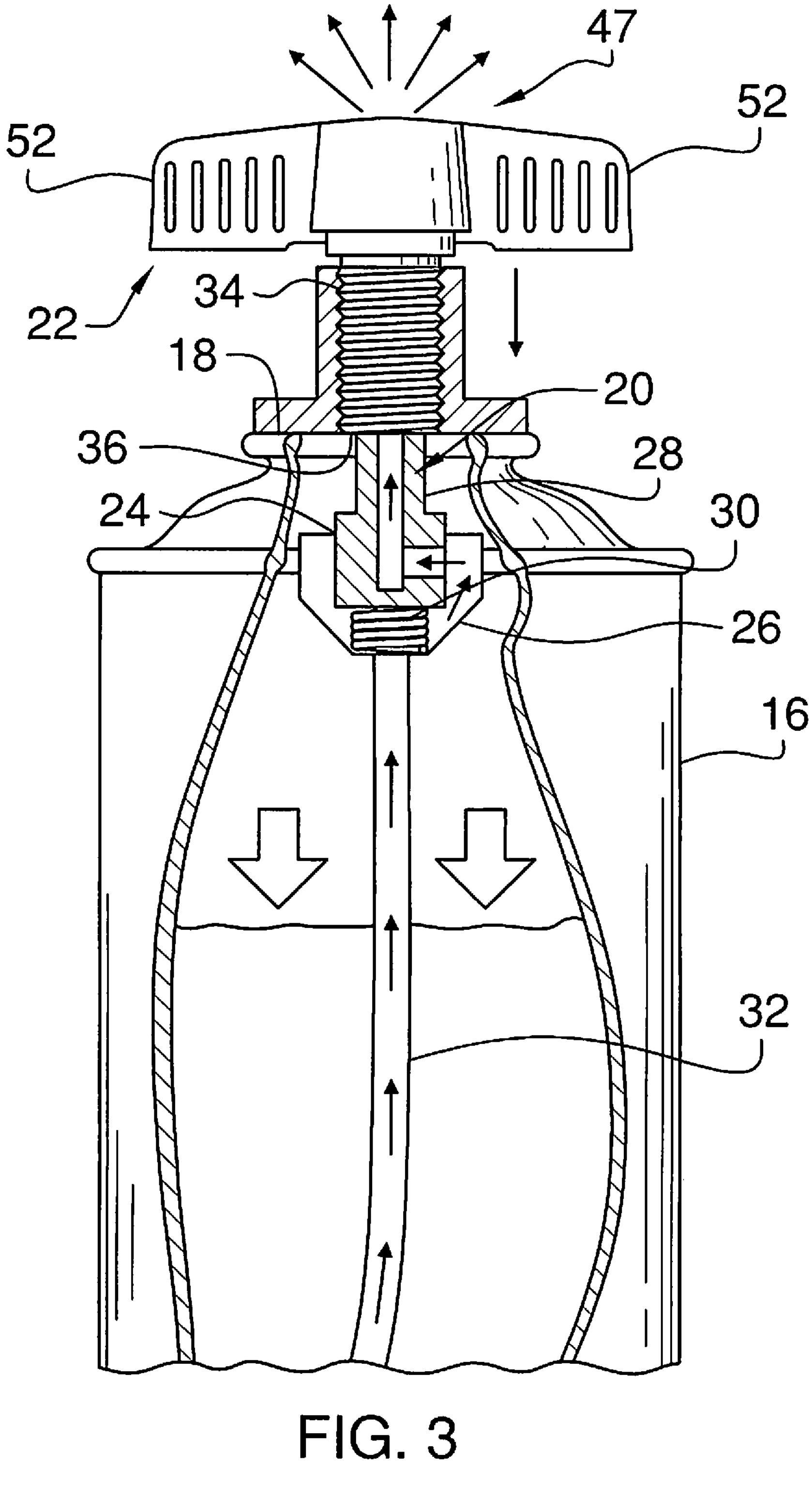
FIG. 3 is a front cut-away view of an embodiment of the disclosure showing an exhaust portion of a valve in an open position.
Figure 4:
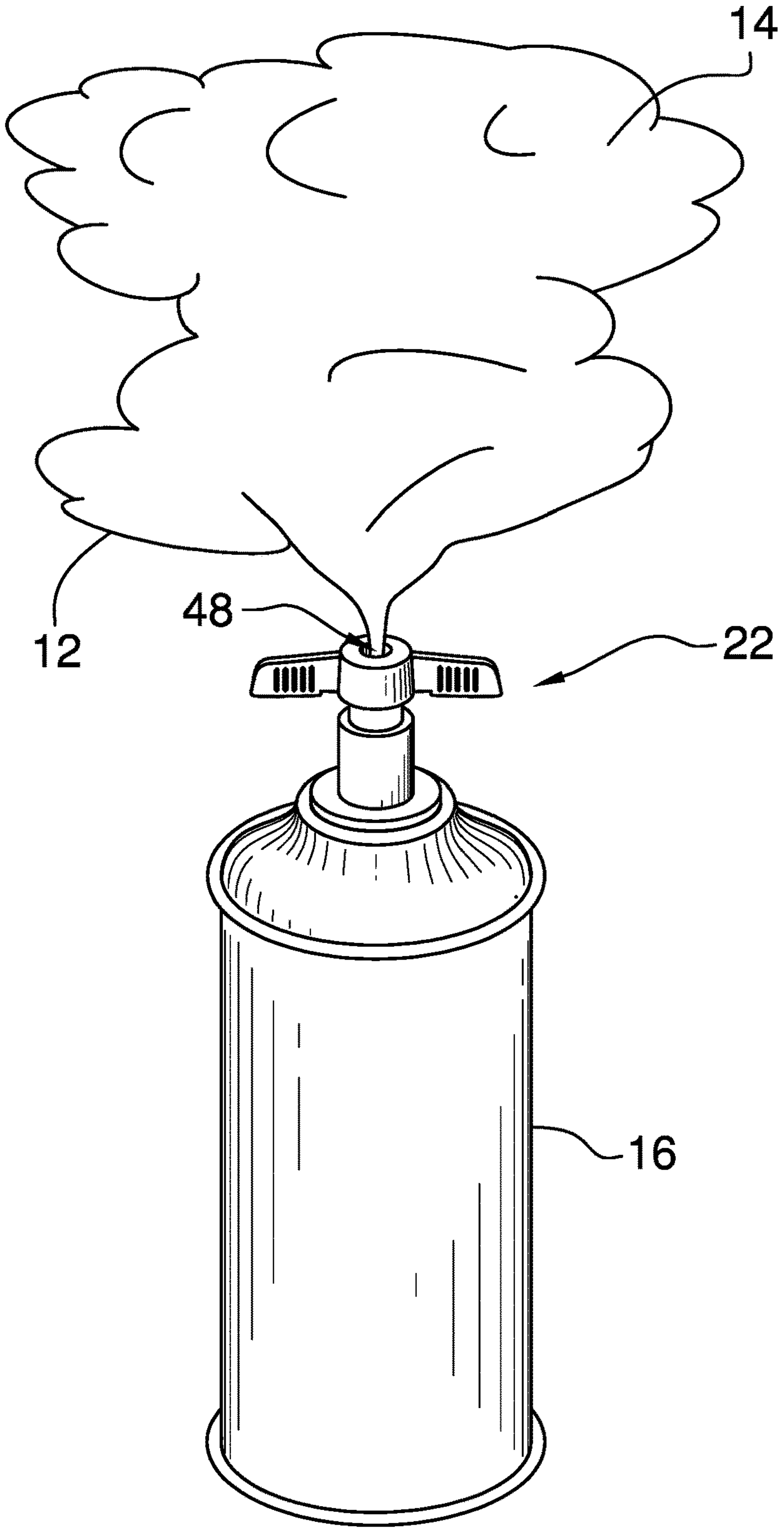
FIG. 4 is a perspective in-use view of an embodiment of the disclosure.

With reference now to the drawings, and in particular to FIGS. 1 through 4 thereof, a new disinfectant device embodying the principles and concepts of an embodiment of the disclosure and generally designated by the reference numeral 10 will be described.

As best illustrated in FIGS. 1 through 4, the aerosolized disinfectant assembly 10 generally comprises an aerosol 12 that includes a chemical disinfectant 14. A canister 16 is provided and the aerosol 12 is contained under pressure in the canister 16. The canister 16 has a top end 18 and the top end 18 has an opening 20 extending into an interior of the canister 16. The canister 16 is positionable on a floor in a middle of a room and the canister 16 may be an aerosol 12 canister 16 of any conventional design. The aerosol 12 may be a pressurized aerosol 12 of any conventional design and the chemical disinfectant 14 may be a gaseous disinfectant, an atomized fluid disinfectant and any other chemical disinfectant that can be delivered via an aerosol 12. Moreover, the chemical disinfectant 14 may have anti-bacterial and anti-viral properties.

A fogger 22 is coupled to the canister 16 and the fogger 22 is in fluid communication with an interior of the canister 16. The fogger 22 is positionable in an open position thereby facilitating the aerosol 12 to be released from the canister 16 and into the room. In this way the chemical disinfectant 14 is distributed around the room to disinfect the room. The room may be a room that has been exposed to an infectious disease, such as a classroom in a school or the like, and the room may need to be disinfected for the purposes of containing an outbreak of the infectious disease.

The fogger 22 comprises a valve 24 that has an intake portion 26 and an exhaust portion 28 that is slidably coupled to the intake portion 26. The intake portion 26 is positioned in the opening 20 in the top end 18 of the canister 16 such that the intake portion 26 closes the opening 20. Moreover, the intake portion 26 is in fluid communication with the interior of the canister 16. The exhaust portion 28 is positionable between a closed position and an open position. The exhaust portion 28 is fluidly discrete from the intake portion 26 when the exhaust portion 28 is positioned in the closed position to retain the aerosol 12 in the canister 16. Alternatively, the exhaust portion 28 is in fluid communion with the intake portion 26 when the exhaust portion 28 is positioned in the open position to release the aerosol 12 from the canister 16.

A biasing member 30 is positioned within the valve 24 and the biasing member 30 is positioned between the intake portion 26 and the exhaust portion 28. The biasing member 30 biases the exhaust portion 28 into the closed position and the biasing member 30 may comprise a spring or the like. A tube 32 is fluidly coupled to the intake portion 26 and extends downwardly into the canister 16. The tube 32 directs the aerosol 12 into the valve 24 when the exhaust portion 28 is positioned in the open position.

A sleeve 34 is provided that has a first end 36, a second end 38 and an outer surface 40 extending therebetween. The outer surface 40 is threaded and the sleeve 34 is positioned on the top end 18 of the canister 16 having the first end 36 being aligned with the opening 20 in the top end 18. The exhaust portion 28 of the valve 24 is coupled to the first end 36 of the sleeve 34 having the sleeve 34 extending upwardly from the top end 18 of the canister 16. A flange 42 is provided that has a cylinder 44 and a lip 45, and the cylinder 44 has an interior surface 46. The lip 45 abuts the top end 18 of the cylinder 44 and the outer surface 40 of the sleeve 34 threadably engages the interior surface 46 of the cylinder 44. Thus, the sleeve 34 is urged upwardly and downwardly in the flange 42 when the sleeve 34 is rotated.

A collar 47 is provided and the collar 47 is coupled to the second end 38 of the sleeve 34. The collar 47 has an inside surface 48 forming an opening 49 extending through the collar 47 and an outside surface 50. The opening 49 in the collar 47 is aligned with the second end 38 of the sleeve 34 and the opening 49 in the collar 47 releases the aerosol 12 when the exhaust portion 28 is positioned in the open position. Additionally, the collar 47 has a pair of wings 52 extending outwardly from the outside surface 50 for gripping. The collar 47 is rotatable in a first direction thereby urging the sleeve 34 to travel downwardly in the flange 42. In this way the sleeve 34 urges the exhaust portion 28 into the open position for releasing the aerosol 12 from the canister 16.

In use, the canister 16 is positioned on the floor near a middle of the room when the room needs to be disinfected due to being exposed to an infectious disease or any other conceivable reason that a room would need to be disinfected. The collar 47 is rotated in the first direction to open the valve 24. Thus, the aerosol 12 is released from the canister 16 to be evenly diffused throughout the room. In this way the chemical disinfectant 14 in the aerosol 12 contacts all surfaces in the room thereby disinfecting the room without requiring one or more individuals to manually disinfect the room. The room is left closed off for a selected amount of time to allow the chemical disinfectant 14 to fully disinfect the room.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An aerosolized disinfectant assembly for releasing an aerosolized disinfectant wherein said aerosolized disinfectant is configured to disinfect a room, said assembly comprising:

an aerosol including a chemical disinfectant;

a canister having said aerosol being contained within under pressure, said canister having a top end, said top end having an opening extending into an interior of said canister; and a fogger being coupled to said canister and being in fluid communication with an interior of said canister, said fogger being positionable in an open position thereby facilitating said aerosol to be released from said canister and into the room wherein said chemical disinfectant is configured to disinfect the room, said fogger including a valve being in fluid communication with said interior of said canister, a sleeve having a first end, a second end and an outer surface extending therebetween, said outer surface being threaded, said sleeve being positioned on said top end of said canister having said first end being aligned with said opening in said top end, said valve being coupled to said first end of said sleeve having said sleeve extending upwardly from said top end of said canister, a collar being slidably coupled to said second end of said sleeve such that said collar is selectively removable from said second end of said sleeve, rotation of said collar rotating said sleeve when said collar is coupled to said sleeve, said collar having an inside surface forming an opening extending through said collar and an outside surface, said opening in said collar being aligned with said second end of said sleeve said opening in said collar releases said aerosol when said exhaust portion is positioned in said open position.

2. The assembly according to claim 1, wherein said fogger comprises said valve having an intake portion and an exhaust portion being slidably coupled to said intake portion, said intake portion being positioned in said opening in said top end of said canister such that said intake portion closes said opening, said intake portion being in fluid communication with said interior of said canister.

3. The assembly according to claim 2, wherein said exhaust portion is positionable between a closed position and an open position, said exhaust portion being fluidly discrete from said intake portion when said exhaust portion is positioned in said closed position to retain said aerosol in said canister, said exhaust portion being in fluid communion with said intake portion when said exhaust portion is positioned in said open position to release said aerosol from said canister.

4. The assembly according to claim 3, further comprising a tube being fluidly coupled to said intake portion and extending downwardly into said canister, said tube directing said aerosol into said valve when said exhaust portion is positioned in said open position.

5. The assembly according to claim 1, wherein said exhaust portion of said valve is coupled to said first end of said sleeve.

6. The assembly according to claim 5, further comprising a flange having a cylinder and a lip, said cylinder having an interior surface, said lip abutting said top end of said cylinder having said outer surface of said sleeve threadably engaging said interior surface of said cylinder.

7. The assembly according to claim 1, wherein said collar has a pair of wings extending outwardly from said outside surface for gripping, said collar being rotatable in a first direction having said sleeve traveling downwardly in said flange thereby urging said exhaust portion into said open position for releasing said aerosol from said canister.

8. An aerosolized disinfectant assembly for releasing an aerosolized disinfectant wherein said aerosolized disinfectant is configured to disinfect a room, said assembly comprising:

an aerosol including a chemical disinfectant;

a canister having said aerosol being contained within under pressure, said canister having a top end, said top end having an opening extending into an interior of said canister, said canister being positionable on a floor in a middle of a room; and a fogger being coupled to said canister and being in fluid communication with an interior of said canister, said fogger being positionable in an open position thereby facilitating said aerosol to be released from said canister and into the room wherein said chemical disinfectant is configured to disinfect the room, said fogger comprising:

a valve having an intake portion and an exhaust portion being slidably coupled to said intake portion, said intake portion being positioned in said opening in said top end of said canister such that said intake portion closes said opening, said intake portion being in fluid communication with said interior of said canister, said exhaust portion being positionable between a closed position and an open position, said exhaust portion being fluidly discrete from said intake portion when said exhaust portion is positioned in said closed position to retain said aerosol in said canister, said exhaust portion being in fluid communion with said intake portion when said exhaust portion is positioned in said open position to release said aerosol from said canister;

a biasing member being positioned within said valve, said biasing member being positioned between said intake portion and said exhaust portion, said biasing member biasing said exhaust portion into said closed position;

a tube being fluidly coupled to said intake portion and extending downwardly into said canister, said tube directing said aerosol into said valve when said exhaust portion is positioned in said open position;

a sleeve having a first end, a second end and an outer surface extending therebetween, said outer surface being threaded, said sleeve being positioned on said top end of said canister having said first end being aligned with said opening in said top end, said exhaust portion of said valve being coupled to said first end of said sleeve having said sleeve extending upwardly from said top end of said canister;

a flange having a cylinder and a lip, said cylinder having an interior surface, said lip abutting said top end of said cylinder having said outer surface of said sleeve threadably engaging said interior surface of said cylinder; and a collar being slidably coupled to said second end of said sleeve such that said collar is selectively removable from said second end of said sleeve, rotation of said collar rotating said sleeve when said collar is coupled to said sleeve, said collar having an inside surface forming an opening extending through said collar and an outside surface, said opening in said collar being aligned with said second end of said sleeve said opening in said collar releases said aerosol when said exhaust portion is positioned in said open position, said collar having a pair of wings extending outwardly from said outside surface for gripping, said collar being rotatable in a first direction having said sleeve traveling downwardly in said flange thereby urging said exhaust portion into said open position for releasing said aerosol from said canister.

* * * * *